(12) United States Patent  (10) Patent No.: US 8,781,060 B2
Kondo  (45) Date of Patent: Jul. 15, 2014

(54) EXPOSURE CONDITION PROCESSING METHOD OF X-RAY CT APPARATUS AND X-RAY CT APPARATUS

(75) Inventor: Gen Kondo, Otawara (JP)

(73) Assignees: Kabushiki Kaisha Toshiba, Tokyo (JP); Toshiba Medical Systems Corporation, Otawara-shi (JP)

( * ) Notice: Subject to any disclaimer, the term of this patent is extended or adjusted under 35 U.S.C. 154(b) by 421 days.

(21) Appl. No.: 13/195,334

(22) Filed: Aug. 1, 2011

(65) Prior Publication Data

US 2012/0039432 A1  Feb. 16, 2012

(30) Foreign Application Priority Data

Aug. 10, 2010 (JP) ................................ 2010-179178

(51) Int. Cl.
*A61B 6/00* (2006.01)
(52) U.S. Cl.
USPC ............................................................ 378/4
(58) Field of Classification Search
USPC .............................................. 378/4–20, 901
See application file for complete search history.

(56) References Cited

U.S. PATENT DOCUMENTS

2010/0232566 A1  9/2010 Hirokawa et al.

FOREIGN PATENT DOCUMENTS

| JP | 7-79965 | 3/1995 |
| JP | 2008-148886 | 7/2008 |
| WO | WO 2009/020136 A1 | 2/2009 |

OTHER PUBLICATIONS

Japanese Office Action dated Feb. 12, 2014, in Japanese Patent Application No. 2010-179178.

*Primary Examiner* — Courtney Thomas
(74) *Attorney, Agent, or Firm* — Oblon, Spivak, McClelland, Maier & Neustadt, L.L.P.

(57) ABSTRACT

An exposure condition processing method for an X-ray CT apparatus according to the embodiment includes: a step in which a first X-ray emitting condition and a second X-ray emitting condition for the X-ray CT apparatus are input to a processor; a step in which the processor, based on the first X-ray emitting condition and the second X-ray emitting condition, acquires interval times for switching the first X-ray scanning with the first X-ray emitting condition, and the second X-ray scanning with the second X-ray emitting condition; a step in which the processor, based on the rotation speed of a gantry in the X-ray CT apparatus that is previously stored in a memory and the interval times, calculates the frequency of intermittent emission of an X-ray, with respect to the rotation speed of the gantry.

15 Claims, 7 Drawing Sheets

EXPOSURE CONDITION PROCESSING METHOD OF X-RAY CT APPARATUS AND X-RAY CT APPARATUS

CROSS-REFERENCE TO RELATED APPLICATION

This application is based upon and claims the benefit of priority from Japanese Patent Application No. 2010-179178, filed Aug. 10, 2010; the entire contents of which are incorporated herein by reference.

FIELD

Embodiments of the present invention relate to an exposure condition processing method of an X-ray CT apparatus; and an X-ray CT apparatus.

BACKGROUND

An X-ray CT apparatus is a diagnostic imaging apparatus that emits X-rays, detects the X-rays which have penetrated through a subject, and reconstructs the image of the subject from the projection data showing the intensity of the detected X-rays.

As a scanning method using the X-ray CT apparatus, for example, dynamic volume scanning and helical scanning are well known.

Volume scanning refers to a method in which a plurality of detectors (for example, several hundred rows) are provided, and by rotating these detectors around a fixed subject, for an organ approximately the size of a heart, 3-dimensional data thereof can be acquired with one scan. Moreover, dynamic scanning refers to a method in which movement of the subject is photographed by performing X-ray scanning on the subject into which a contrast agent is injected. Dynamic volume scanning refers to the combination of these methods.

Moreover, helical scanning refers to a method in which while scanning is performed with detectors that are continuously rotated at a high speed, by simultaneously moving the bed on which the subject is placed at a constant speed, a plurality of cross-sectional scans are completed in a short period of time.

Moreover, a well-known method referred to as the dual energy method can be used in combination with these scanning methods.

This method sequentially performs, with respect to the same site of the subject, X-ray scanning with a high tube voltage and X-ray scanning with a low tube voltage, generating a difference image based on the two X-ray image data obtained using X-rays of different radiation quality.

DETAILED DESCRIPTION

An exposure condition processing method of an X-ray CT apparatus according to the embodiment has a step in which a first X-ray emitting condition for the X-ray CT apparatus and a second X-ray emitting condition, which is different from the first X-ray emitting condition, are input to a processor. Furthermore, it involves a step in which the processor, based on the first X-ray emitting condition and the second X-ray emitting condition, acquires interval times for switching the first X-ray scanning, resulting from the first X-ray emitting condition, and the second X-ray scanning, resulting from the second X-ray emitting condition. Furthermore, it involves a step in which the processor, based on the rotation speed of a gantry in the X-ray CT apparatus and the interval times, which are previously stored in a memory, calculates the frequency of intermittent emission of an X-ray, with respect to the rotation speed of the gantry.

(Device Configuration)

Figure 1:
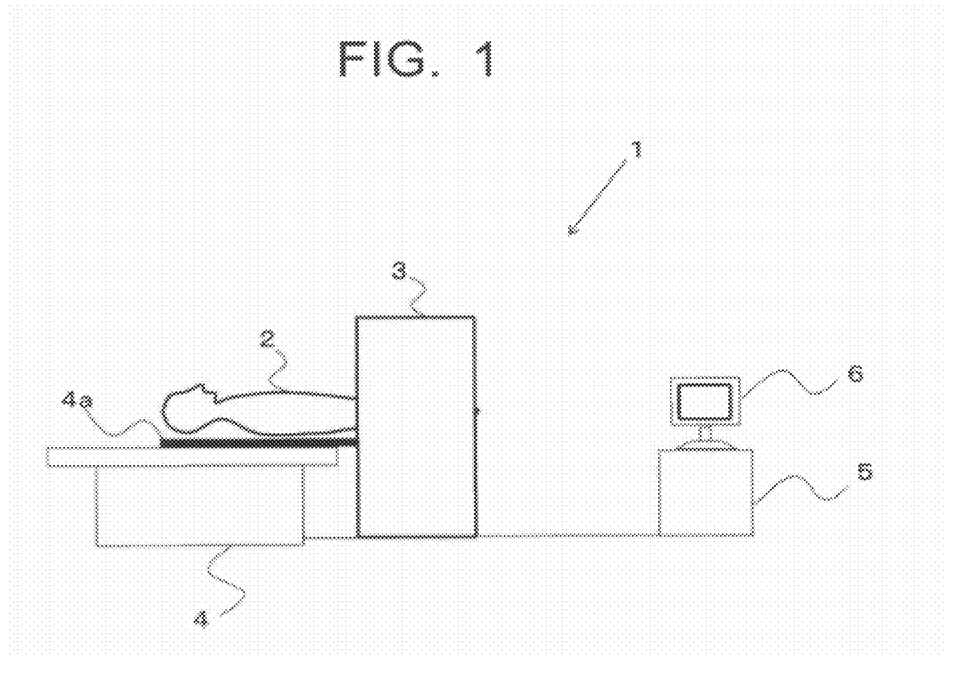
FIG. 1 is an outline view of an X-ray CT apparatus according to the first and second embodiments.
Figure 2:
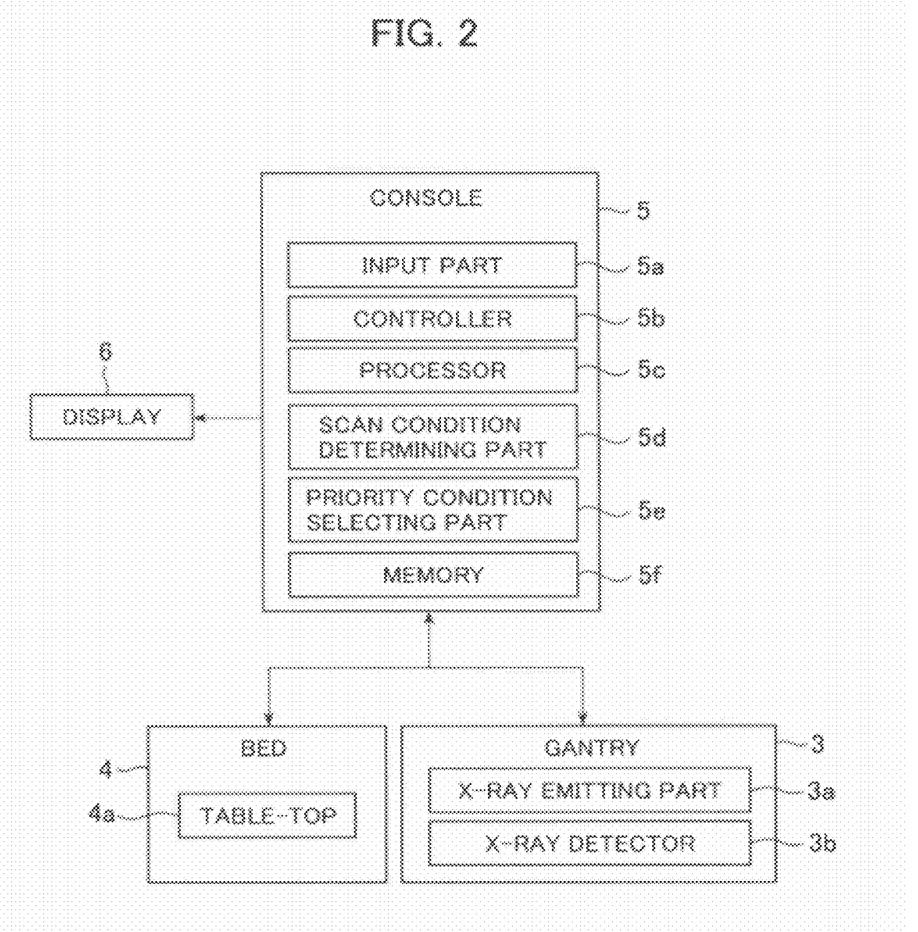
FIG. 2 is a block diagram of the X-ray CT apparatus according to the first and second embodiments.

First, using FIG. 1 and FIG. 2, the configuration of an X-ray CT apparatus 1 that is common for a first embodiment and a second embodiment is explained.

The X-ray CT apparatus 1 is a diagnostic imaging apparatus that detects X-rays which have penetrated through a subject by emitting X-rays, and reconstructs the image of the subject from the projection data showing the intensity of the detected X-rays. This X-ray CT apparatus 1 is provided with a gantry 3, a bed 4, and a console 5.

The gantry 3 performs irradiation of X-rays and detection of the X-rays that has penetrated a subject 2. Housed inside the gantry 3 are an X-ray emitting part 3a having an X-ray tube that irradiates X-rays as a high voltage is applied from a high-voltage generator, not shown in the figures, and an X-ray detector 3b that detects the X-rays penetrating the subject 2. Note that the X-ray emitting part 3a and the X-ray detector 3b are disposed on a rotation base, not shown in the figures. The rotation base is disposed inside the gantry 3 so as to rotate around the subject 2. In the present embodiment, this "rotation of the rotation base" may be referred to as being the same as "rotation of the gantry 3." For example, "the rotation speed of the gantry" refers to the rotation speed of the rotation base.

The bed 4 has a table-top 4a. The subject 2 is disposed on the table-top 4a. The table-top 4a, based on a command from a controller 5b, which is described subsequently, is constituted so as to be movable with respect to the bed 4, while disposing the subject 2.

An input part 5a for external input is disposed on the console 5.

Moreover, the controller 5b that controls the actions for the entire X-ray CT apparatus is disposed on the console 5. Further, disposed on the console 5 is a processor 5c that processes an X-ray exposure condition, based on an input command from the input part 5a, and performs reconstruction processing of X-ray detection results from the X-ray detector 3b for an X-ray image. Processing of the X-ray exposure condition by the processor 5c is described subsequently.

Moreover, disposed on the console 5 is a scan condition determining part 5d that determines a scan condition (described subsequently), based on the input command from the input part 5a.

Moreover, disposed on the console 5 is a priority condition selecting part 5e that selects a priority condition (described subsequently) stored in a memory 5f, which is described subsequently, based on the input command from the input part 5a. Moreover, disposed on the console 5 is a memory 5f to which various conditions applicable to the X-ray scanning, such as the rotation speed of the gantry (described subsequently), are stored.

A display 6 is connected to the console 5 and displays the results of processing from the processor 5c.

(Explanation Regarding the Dual Energy Method)

Figure 3:
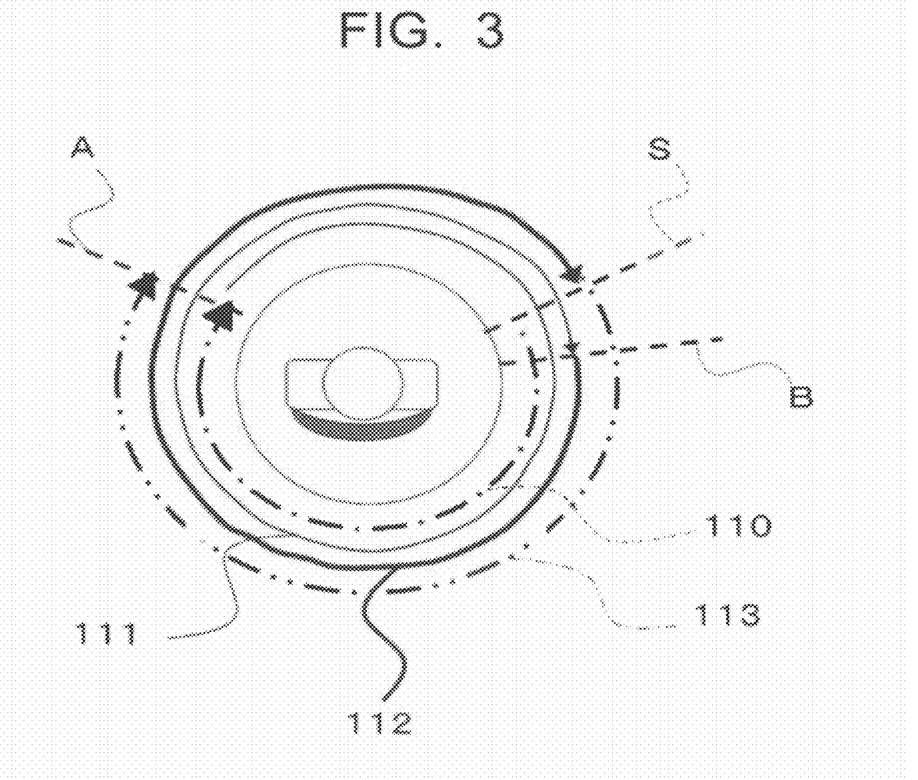
FIG. 3 is an explanation drawing regarding a dual energy method according to the first and second embodiments.

Next, using FIG. 3, the dual energy method, which is an X-ray scanning method used in the first embodiment and the second embodiment, is explained.

Note that in the present embodiment, "half reconstruction" refers to a method in which, when the gantry 3 (rotation base) rotates one turn, data for a half turn of the gantry 3 and data for a fan angle (approximately ⅔ turn) of the X-ray detector 3b are acquired, and in which reconstruction of the X-ray image is performed based on the data. "Full reconstruction" refers to a method in which reconstruction of the X-ray image is performed based on the data acquired when the gantry 3 rotates one turn. The "Slow kV switching method" refers to a method in which, as the gantry 3 rotates one turn, the tube voltage and tube current for the X-ray scanning are switched. For example, with half reconstruction, subject's data is acquired in approximately ⅔ turn, and with the remaining ⅓ turn, the X-ray emitting condition is switched. The "X-ray emitting condition" refers to the current value (mA) and voltage value (kV) necessary to emit a predefined X-ray. "Scan" refers to a step in which the X-ray is emitted with respect to the subject under the first X-ray emitting condition, up to a step in which the X-ray can be emitted with respect to the subject under the second X-ray emitting condition. That is, not only does scanning involve irradiation of the X-ray, but it also involves a switching step of the current value and voltage value from the first X-ray emitting condition to the second X-ray emitting condition, and a step for performing trajectory specification (described subsequently). "Scan condition" refers to the X-ray emitting condition, as well as the exposure range within which X-ray scanning is performed, the moving speed of the bed 4 (the table-top 4a), reconstruction condition (half reconstruction or full reconstruction), effective field of view, slice thickness, etc. These values are arbitrarily set by testers. The "trajectory specification" is a method for specifying, when scanning under the first and second X-ray emitting conditions, which are different from each other, a starting point in order to start scanning with the first X-ray emitting condition and a scan with the second X-ray emitting condition from the same angle (angle with respect to a predefined reference direction). By differential processing the data based on the respective X-ray emitting conditions obtained as photography is started at the same angle, the X-ray image can be reconstructed such that effects of artifact are eliminated. The "trajectory specification angle S [rad]" refers to the angle at which irradiation is started with the first X-ray emitting condition and the second X-ray emitting condition (angle with respect to a predefined reference direction). This angle can be determined arbitrarily. The "switching start angle A [rad]" refers to the angle at which switching from the first X-ray emitting condition (or from the second X-ray emitting condition) to the second X-ray emitting condition (or to the first X-ray emitting condition) is started (angle with respect to a predefined reference direction). This angle is defined by determining the trajectory specification angle S and the reconstruction condition (full reconstruction or half reconstruction). The "switching completion angle B [rad]" refers to the angle at which switching of the X-ray emitting condition that is started at the switching start angle completes (angle with respect to a predefined reference direction). This angle is decided by the X-ray emitting condition. The "first tube voltage $X_{kv}$ 1 [kV]" and "first tube current $X_{mA}$ 1 [mA]" are the tube voltage and tube current constituting the first X-ray emitting condition. The "second tube voltage $X_{kv}$ 2 [kV]" and "second tube current $X_{mA}$ 2 [mA]" are the tube voltage and tube current constituting the second X-ray emitting condition. "Interval times Tc [s]" is the time required for switching from the first X-ray emitting condition to the second X-ray emitting condition. During this time, irradiation of the X-ray is stopped. This value is determined from a table, etc., based on the combination of the first and second X-ray emitting conditions. The "rotation speed of the gantry R [s/r]" is the time taken for the gantry 3 (rotation base) to rotate one turn. The "full reconstruction view number Nf (R)" is the amount of X-ray image data that may be obtained when the gantry 3 rotates one turn. This is the value determined from a table, etc., based on the rotation speed of the gantry. The "reconstruction view number Nh (R)" is the amount of X-ray image data that is defined by the scan condition and the rotation speed of the gantry. For example, for cases of half reconstruction, the value is obtained from Nh (R)≈Nf (R)×⅔. "Frequency of intermittent emission Y [r]" shows how many times the gantry 3 rotates in order to perform one scan. The "number of X-ray emissions" is the number of times that X-ray emission (the number of scans) is necessary in order to acquire desired the X-ray image data. For example, if it is set to "20 scans with the dual energy method," it requires X-ray irradiation for 20 times (10 scans with the first X-ray emitting condition and 10 scans with the second X-ray emitting condition). The "priority condition" refers to, for the display of the results of X-ray imaging, a determination condition for cases in which priority is placed on a certain display mode. For example, when a tester would like to prioritize contrast, "contrast" is selected as the priority condition. Moreover, when the tester would like to prioritize time resolution, "time resolution" is selected as the priority condition.

FIG. 3 shows a measurement state for a trajectory specification dual energy scan for half reconstruction.

First, from the previously defined trajectory specification angle S, a first scan 110 is started based on the first X-ray emitting condition. When the first scan 110 is started, the gantry 3 starts the rotation, and at the same time, the X-ray is emitted from the X-ray emitting part 3a to the subject 2 based on the first X-ray emitting condition.

Since in the present embodiment, the half reconstruction condition is applied, the first scan 110 is performed up to the position of the switching start angle A. That is, the first scan 110 is performed by turning approximately ⅔ clockwise (right-hand turn) from the trajectory specification angle S to the switching start angle A.

Subsequently, the first X-ray emitting condition is switched to the second X-ray emitting condition. Since it takes a predefined time (the interval times Tc) for this action, during this time, the gantry 3 rotates around the subject 2, in the state in which the X-ray is not emitted. In FIG. 3, the rotation according to this switching action is shown as an X-ray switch rotation 111.

After switching from the first X-ray emitting condition to the second X-ray emitting condition completed at the switching completion angle B, rotation of the gantry 3 is required in order to match the position at which irradiation is started with the second X-ray emitting condition to the trajectory specification angle S. In FIG. 3, the rotation according to this trajectory matching is shown as the trajectory matching rotation 112.

When the X-ray emitting part 3a inside the gantry 3 reaches the trajectory specification angle S resulting from the trajectory matching rotation 112, irradiation of the X-ray is started with the second X-ray emitting condition. In FIG. 3, the X-ray scanning under the second X-ray emitting condition is shown as the second scan 113.

After X-ray scanning is performed for approximately ⅔ turn with the second scan, in order to perform a scan with the first X-ray emitting condition again, the X-ray emitting condition is switched and trajectory matching is performed. Accordingly, based on the X-ray image data obtained by scanning the predefined exposure range, the X-ray image is reconstructed and is displayed on the display 6.

In this way, according to the trajectory specification dual energy scan for half reconstruction, by performing differential processing of the data based on the first X-ray emitting condition and the data based on the second X-ray emitting condition, obtained by starting at the same angle, the X-ray image can be reconstructed such that artifact effects are eliminated.

Note that for cases of full configuration, the first scan 110 and the second scan 113 change to one rotation and are changed after going through the X-ray switch rotation 111 and the trajectory matching rotation 112.

Moreover, when performing half reconstruction using the Slow kV switching method, in the rotation from the switching start angle A to the trajectory specification angle S, the X-ray emitting condition is switched. In this case, rotation from the switching start angle A to the trajectory specification angle S falls under the X-ray switch rotation 111 and the trajectory matching rotation 112.

(First Embodiment)

Figure 4:
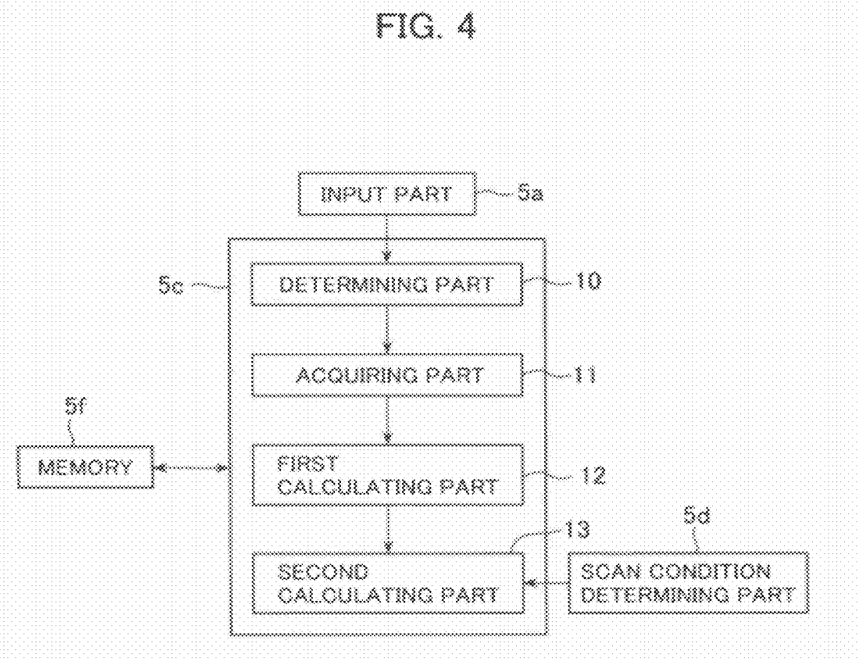
FIG. 4 is a block diagram of a processor according to the first embodiment.
Figure 5:
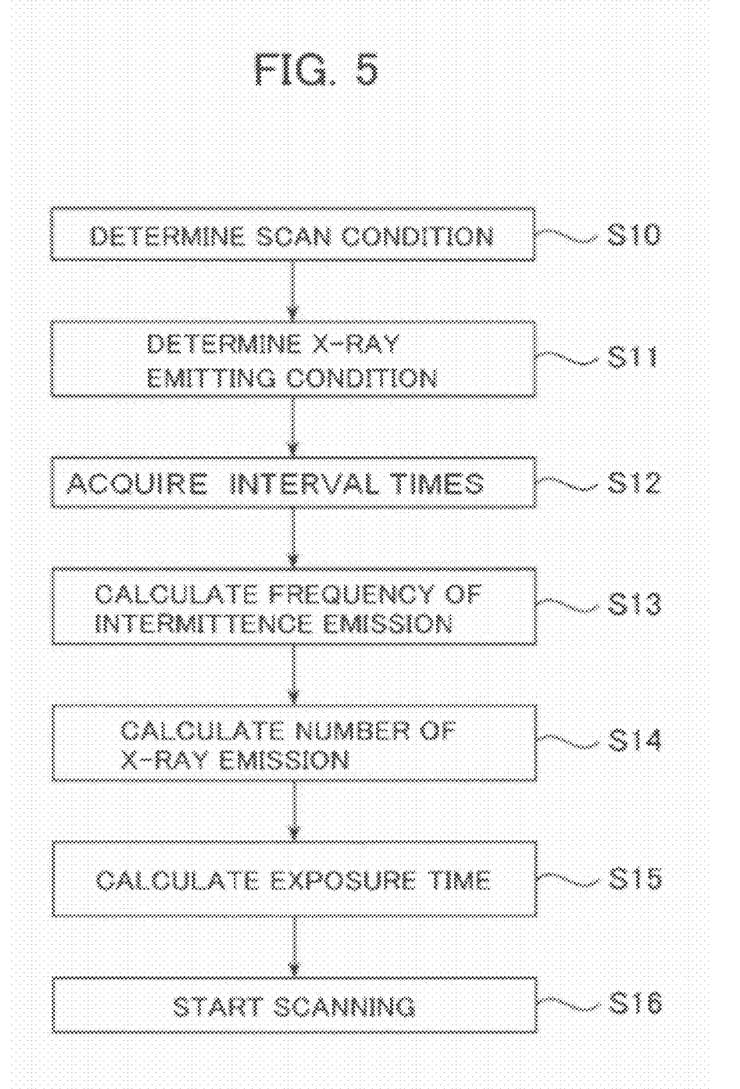
FIG. 5 is a flowchart of the X-ray CT apparatus according to the first embodiment.

Next, using FIG. 4 and FIG. 5, the first embodiment is explained.

The present embodiment describes the dual energy method scan for full reconstruction.

As shown in FIG. 4, the processor 5c according to the present invention has a determining part 10, an acquiring part 11, a first calculating part 12, and a second calculating part 13. Note that the processor 5c performs processing to reconstruct the X-ray image for displaying on the display 6, based on the X-ray detection results from the X-ray detector 3b; however, the processing is generally known; hence, a detailed explanation is omitted.

The determining part 10 determines the first X-ray emitting condition and the second X-ray emitting condition for performing X-ray scanning with the dual energy method, resulting from the input related to the X-ray emitting condition from the input part 5a. This input is performed as the tester arbitrarily selects from the plurality of X-ray emitting conditions displayed on the display 6, and as input with the input part 5a. Note that as the tester inputs arbitrary numerical values (current value and/or voltage value) with the input part 5a, based on the input, as the determining part 10 reads out the X-ray emitting condition corresponding to the input from the plurality of X-ray emitting conditions previously stored in the memory 5f, it is also possible to determine the X-ray emitting condition.

The acquiring part 11 acquires interval times, based on the first X-ray emitting condition and the second X-ray emitting condition determined at the determining part 10, for switching the first X-ray scanning, resulting from the first X-ray emitting condition, and the second X-ray scanning, resulting from the second X-ray emitting condition. Interval times is acquired based on a table, which is stored in the memory 5f, which describes the relationship between the interval times and X-ray emitting conditions (the first X-ray emitting condition and second X-ray emitting condition). That is, when the acquiring part 11 receives information regarding the X-ray emitting condition from the determining part 10, it reads out the table in the memory 5f, specifies the interval times corresponding to this X-ray emitting condition, and acquires this interval times value.

The first calculating part 12 calculates the frequency of intermittent emission of X-rays for the rotation speed of the gantry based on the rotation speed of the gantry and the interval times of the gantry 3. The plurality of rotation speeds of the gantry 3 is stored, for example, in the memory 5f. Moreover, resulting from the input by the tester, etc., any one of the rotation speeds of the gantry is selected. For calculation of the frequency of intermittent emission, Formula (6) or Formula (7), which are described subsequently, are used. That is, the first calculating part 12 performs arithmetic processing of the value of the interval times acquired from the acquiring part 11 and the rotation speed of the gantry selected by the tester based on Formula (6) or Formula (7), thereby calculates the frequency of intermittent emission.

The second calculating part 13 calculates the exposure time for sequentially performing the first X-ray scanning and second X-ray scanning, based on the rotation speed of the gantry 3, the frequency of intermittent emission calculated at the first calculating part 12, and the number of X-ray emissions during the X-ray scanning with the X-ray CT apparatus. Note that the number of X-ray emissions is determined at the scan condition determining part 5d, based on the exposure range input by the input part 5a, the rotation speed, the slice thickness, and a scan condition such as the helical pitch for cases of helical scanning.

Next, using FIG. 5, the X-ray scanning action of the dual energy method, using the X-ray CT apparatus 1, is explained. Note that step numbers in FIG. 5 are shown as "S numbers."

First, a tester (physician, etc.) operates the input part 5a, and inputs the scan condition. The scan condition determining part 5d determines the scan condition based on the input (S10). For example, for cases in which the condition of the exposure range and the slice thickness are input, when it is possible to perform X-ray scanning with the condition (within the exposure range in which the photography can be performed with the X-ray CT apparatus 1, etc.), the scan condition determining part 5d determines the scan condition.

Moreover, the scan condition determining part 5d transmits the signals to the controller 5b so as to perform X-ray scanning under the condition. The controller 5b executes X-ray scanning according to the condition.

Next, based on the input of the input part 5a performed by the tester (physician, etc.), the determining part 10 determines the first X-ray emitting condition and the second X-ray emitting condition (S11).

The first X-ray emitting condition is constituted from the "first tube voltage $X_{kv}$ 1 [kV]" and "first tube current $X_{mA}$ 1 [mA]." The second X-ray emitting condition is constituted from the "second tube voltage $X_{kv}$ 2 [kV]" and "second tube current $X_{mA}$ 2 [mA]." These values can be arbitrarily set by the tester in the operating range of the X-ray emitting part 3a (within the range of the maximum current (voltage) and the minimum current (voltage) for X-ray emitting part 3a). Moreover, the memory 5f may be stored, in advance, a plurality of values in a selectable manner.

Next, the acquiring part 11 acquires the interval times Tc, based on the first X-ray emitting condition and the second X-ray emitting condition, which are determined at S11. The interval times Tc is uniquely determined, with respect to the first X-ray emitting condition and the second X-ray emitting condition. That is, the interval times Tc, when the first X-ray emitting condition and the second X-ray emitting condition are determined, is uniquely acquired based on the table stored in the memory 5f.

Next, the first calculating part 12 calculates the frequency of intermittent emission with respect to the rotation speed of the gantry R from the interval times Tc acquired at S12 and the rotation speed of the gantry R that is determined based on the selection by the tester (S13).

Here, the formula showing a relationship between the interval times Tc, the rotation speed of the gantry R, and the frequency of intermittent emission Y is explained in detail, using FIG. 3.

In FIG. 3, an angle SA required to move from the trajectory specification angle S to the switching start angle A is shown in the following Formula (1), using the full reconstruction view number Nf and the reconstruction view number Nh.

[Formula 1]

$$SA = 2\pi \times \frac{Nh}{Nf} \tag{1}$$

Moreover, in FIG. 3, the angle AB required to move from the switching start angle A to the switching completion angle B is shown in the following Formula (2), using angular speed $\omega$ ($\omega=2\pi/R$) and the interval times Tc.

[Formula 2]

$$AB = \omega \times Tc \tag{2}$$

Moreover, in FIG. 3, the angle BS required to move from the switching completion angle B to the trajectory specification angle S is shown in the following Formula (3), using the rotation speed of the gantry R, the full reconstruction view number Nf, the reconstruction view number Nh, the angular speed $\omega$, and the interval times Tc.

[Formula 3]

$$\begin{aligned}BS &= 2\pi - \mathrm{mod}\left(2\pi \times \frac{Nh}{Nf} + \omega \times Tc, 2\pi\right) \\ &= 2\pi - \mathrm{mod}\left(2\pi \times \frac{Nh}{Nf} + \frac{2\pi}{R} \times Tc, 2\pi\right) \\ &= 2\pi - 2\pi \times \mathrm{mod}\left(\frac{Nh}{Nf} + \frac{Tc}{R}, 1\right)\end{aligned} \tag{3}$$

Note that Y=mod(X,A) means that "Y is the remainder after X is divided by A." What is meant by Y=mod(X,1) is that "Y is a value less than or equal to the decimal point of X."

Next, X-ray scanning is performed with the first X-ray emitting condition (or the second X-ray emitting condition), and the time taken to switch to the second X-ray emitting condition (or the first X-ray emitting condition), that is, the moving time tx in which the angle changes S→A→B→S, is shown in the following Formula (4), using the rotation speed of the gantry R, the full reconstruction view number Nf, the reconstruction view number Nh, the angular speed $\omega$, and the interval times Tc.

[Formula 4]

$$\begin{aligned}tx &= R \times \frac{Nh}{Nf} + Tc + \frac{BS}{\omega} \\ &= R \times \frac{Nh}{Nf} + Tc + \frac{BS \times R}{2\pi} \\ &= R \times \frac{Nh}{Nf} + Tc + R - R \times \mathrm{mod}\left(\frac{Nh}{Nf} + \frac{Tc}{R}, 1\right)\end{aligned} \tag{4}$$

Here, the frequency of intermittent emission Y is shown in the following Formula (5), using the moving time tx during the angle S→A→B→S and the rotation speed of the gantry R.

[Formula 5]

$$Y = \frac{tx}{R} \tag{5}$$

From Formula (4) and Formula (5), the frequency of intermittent emission Y is shown in the following Formula (6).

[Formula 6]

$$Y = \frac{Nh}{Nf} + \frac{Tc}{R} + 1 - \mathrm{mod}\left(\frac{Nh}{Nf} + \frac{Tc}{R}, 1\right) \tag{6}$$

Here, for cases of full reconstruction, it becomes Nh/Nf=1, and the frequency of intermittent emission Y is shown in the following Formula (7).

[Formula 7]

$$Y = 2 + \frac{Tc}{R} - \mathrm{mod}\left(\frac{Tc}{R}, 1\right) \tag{7}$$

That is, at S13, the first calculating part 12 calculates the frequency of intermittent emission based on Formula (6) or Formula (7) above.

For example, as is clear from formula (7), if Tc<R, as the gantry 3 rotates 2 turns, the first scan and the second scan are performed alternately. In contrast, if Tc>R, as it rotates 3 turns, the first scan and the second scan are performed alternately.

Next, the scan condition determining part 5d calculates the number of X-ray emissions necessary for the X-ray scanning based on the scan condition selected by the tester (S14). Note that with regard to the number of X-ray emissions, it may be determined when the scan condition is determined at S10.

Based on the rotation speed of the gantry R determined based on the selection by the tester, the frequency of intermittent emission calculated at S13, and the number of X-ray emissions calculated at S14, the second calculating part 13 calculates the total time required for the X-ray scanning (exposure time [s]) (S15). The calculated exposure time, for example, after being combined with other test conditions by a display controller, not shown in the figures, is displayed on the display 6. Therefore, the tester is able to figure out the first X-ray emitting condition and the second X-ray emitting condition, which are determined based on the tester's own selection, as well as the exposure time resulting from the rotation speed of the gantry R.

When the tester determines that it is appropriate to conduct tests with the exposure time calculated at S15, the tester inputs with the input part 5a, providing a command to start operating the X-ray CT apparatus 1. Accordingly, as the controller 5b, controls the action of the X-ray CT apparatus 1 based on the condition determined from S10 to S15, the X-ray scanning of the dual energy method is started (S16).

Note that, as above, generally, the plurality of rotation speeds of the gantry are stored in the X-ray CT apparatus. Therefore, it is also possible to calculate the frequency of intermittent emission for all of the rotation speeds of the gantry stored in the X-ray CT apparatus. In this case, it is possible to display a table providing each condition, such as Table 1 shown below, on the display 6 and have the tester select any condition.

TABLE 1

| Exposure condition | R[s/r] | Y[r] | Exposure time [s] |
|---|---|---|---|
| 1 | 0.3 | 3 | 18 |
| 2 | 0.4 | 3 | 24 |
| 3 | 0.5 | 2 | 20 |

In Table 1, for any of these conditions, the X-ray emitting condition is the same. Moreover, the number of X-ray emissions is set to 20 times. Note that each numerical value in Table 1 is for illustrative purposes only, so as to make it easy to understand the present embodiment; hence it is not limited to these.

Because Table 1 is displayed on the display 6, the tester can easily recognize that when the X-ray scanning is performed with the exposure condition "1," X-ray scanning can be performed (time resolution being high) with the shortest exposure time (total exposure time).

On the other hand, for cases in which photography is performed using the helical scanning method, the larger the value of the frequency of intermittent emission Y, the smaller the overlapping section of the X-ray image data taken with each X-ray emitting condition. That is, for cases in which the helical scanning method is used, the larger the frequency of intermittent emission, the smaller the contrast of the X-ray image. Even in cases of this type, based on Table 1 displayed on the display 6, the tester is able to determine whether to select the exposure condition "1" in which time resolution is prioritized or the exposure condition "3" in which contrast is prioritized.

Moreover, based on the input command from the input part 5a, it is also possible to select a time resolution priority or a contrast priority for the priority condition selecting part 5e. In this case, by executing the above processing, it can be constituted so as to display, on the display 6, only the exposure condition corresponding to the previously selected condition.

On the other hand, it is also possible to display on the display 6, so as to recommend the exposure condition matching the previously selected condition. For example, for cases of "time resolution priority," it is possible to display such that the frame for the exposure condition "1" in Table 1 or characters displayed within this frame are displayed in different display colors.

Furthermore, depending on the relationship between the rotation speed of the gantry and the frequency of intermittent emission, the exposure time may be equal. For example, for cases when R=0.4 [s/r] and Y=3, and for cases when R=0.6 [s/r] and Y=2, for both cases, the X-ray is emitted for each 1.2 [s]. Therefore, if the number of X-ray emissions is set to 20 times, for both cases, an exposure time of 24 [s] is required. Even in cases of this type, because a list of the exposure conditions as shown in Table 1 is displayed, the tester can easily select the exposure condition (for cases of R=0.6 [s/r] and Y=2) for prioritizing the contrast. This selection may also be performed automatically, based on the scan condition, etc., determined in advance.

Furthermore, the interval times Tc1 for cases of switching from the first X-ray emitting condition to the second X-ray emitting condition and the interval times Tc2 for cases of switching from the second X-ray emitting condition to the first X-ray emitting condition may differ.

Even in such cases, it is possible to calculate, from Formula (7), the frequency of intermittent emission Y1 and Y2, with respect to each interval times, and calculate the total exposure time based on the rotation speed of the gantry and the number of X-ray emissions. Note that in this case, in Table 1, it is also possible to display both frequencies of intermittent emission Y1 and Y2.

Note that among the items described in Table 1, for the item to be displayed on the display 6, either one may be displayed. Moreover, it is also possible to display the first X-ray emitting condition and the second X-ray emitting condition.

Even for cases of half reconstruction, using Formula (6), it is possible to calculate the exposure time by calculating the frequency of intermittent emission Y.

As above, according to the present embodiment, based on Formula (6) or Formula (7), it is possible to calculate the frequency of intermittent emission of the X-ray and display the exposure condition including this value on the display 6. Therefore, because the tester can arbitrarily select the exposure condition, desired tests can be conducted effectively.

(Second Embodiment)

Figure 6:
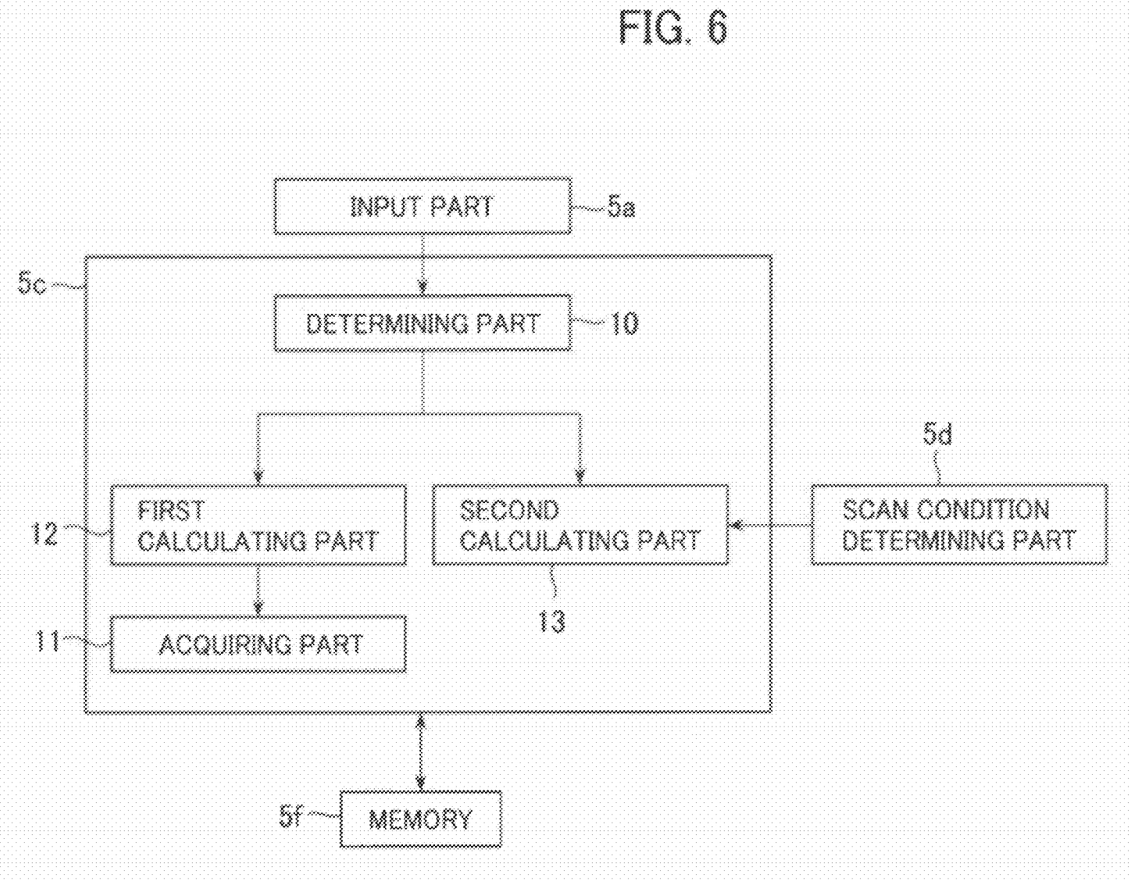
FIG. 6 is a block diagram of a processor according to the second embodiment.
Figure 7:
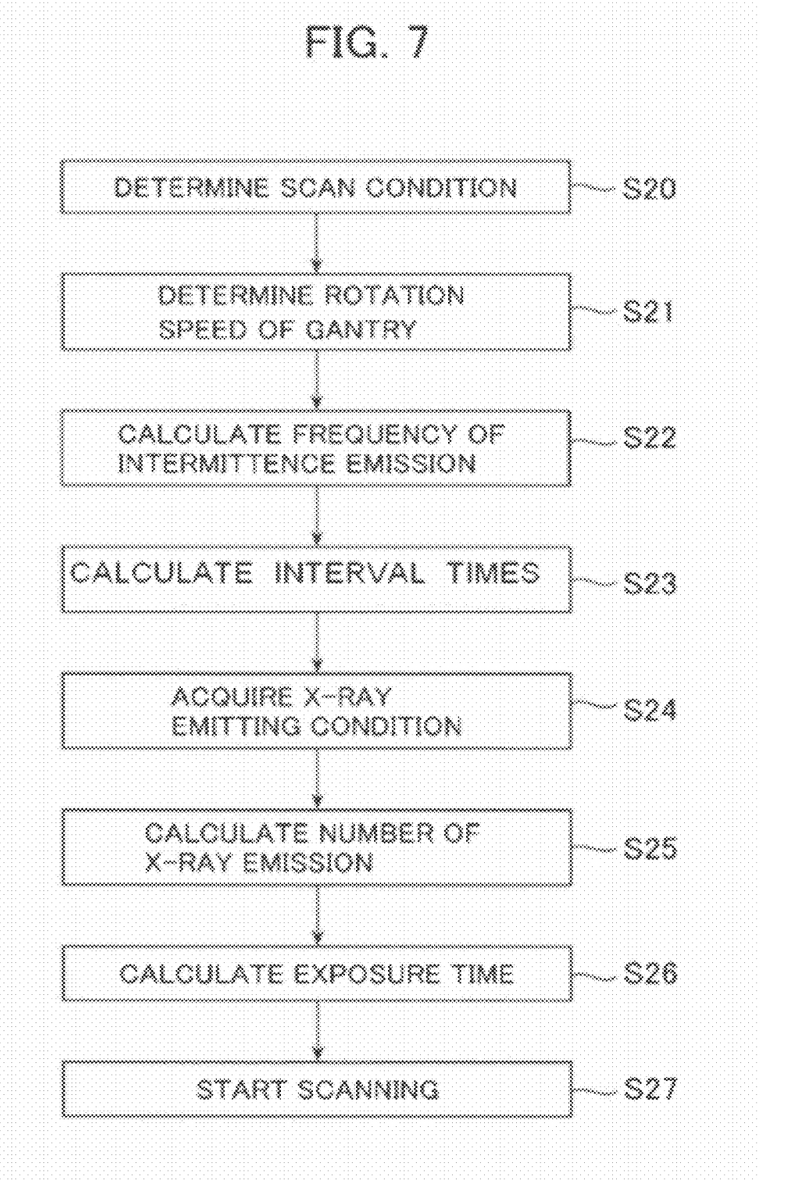
FIG. 7 is a flowchart of the X-ray CT apparatus according to the second embodiment.

Next, using FIG. 6 and FIG. 7, the second embodiment is explained. In the present embodiment, the dual energy method for full reconstruction is described.

As shown in FIG. 6, a processor 5c in the present embodiment, as is the case with the first embodiment, has a determining part 10, an acquiring part 11, a first calculating part 12, and a second calculating part 13. Note that the action of the second calculating part 13 is the same as the first embodiment; hence, an explanation is omitted.

The determining part 10 in the present embodiment determines the rotation speed of the gantry 3 and the frequency of intermittent emission, resulting from the input command from the input part 5a. The input command is arbitrarily selected by a tester, from the plurality of rotation speeds of the gantry or the frequencies of intermittent emission displayed on the display 6, and is carried out as input at the input part 5a. Or, for cases in which a plurality of gantry rotations and the frequencies of intermittent emission with respect thereof are associated and stored in the memory 5f and a rotation speed of the gantry is determined, the frequency of intermittent emission may be uniquely determined.

The first calculating part 12 in the present embodiment, based on the rotation speed of the gantry and the frequency of intermittent emission determined at the determining part 10, calculates the interval times for switching the first X-ray scanning with the first X-ray emitting condition, and the second X-ray scanning with the second X-ray emitting condition. For calculating interval times, Formula (6) or Formula (7) described in the first embodiment is used. That is, the first calculating part 12 performs arithmetic processing with respect to the rotation speed of the gantry and the frequency of intermittent emission, which are determined by the determining part 10, based on Formula (6) or Formula (7), and calculates interval times.

The acquiring part 11 in the present embodiment acquires the first X-ray emitting condition and the second X-ray emitting condition based on the interval times calculated at the first calculating part 12.

As described in the explanation for the first embodiment, the interval times Tc, for cases in which the first X-ray emitting condition and the second X-ray emitting condition are determined, is a value that is uniquely acquired based on the table stored in the memory 5f.

Therefore, from the interval times calculated at the first calculating part 12, the acquiring part 11, based on the table stored in the memory 5f, can uniquely acquire the first X-ray emitting condition and the second X-ray emitting condition. That is, when the acquiring part 11 receives information regarding the interval times Tc from the first calculating part 12, it reads out a table in the memory 5f, specifies the first X-ray emitting condition and the second X-ray emitting condition corresponding to the interval times, and acquires values for the first X-ray emitting condition and the second X-ray emitting condition.

Next, using FIG. 7, the X-ray scanning action for the dual energy method is explained, using the X-ray CT apparatus 1. Note that the step number in FIG. 7 is shown in "S numbers."

First, as a tester (physician, etc.) operates the input part 5a and inputs the scan condition, the scan condition determining part 5d determines the scan condition (S20). For example, for cases in which input is performed with regard to the condition of the exposure range and the slice thickness, the signals are transmitted to the controller 5b so as to perform X-ray scanning under the condition. The controller 5b executes X-ray scanning under the condition. Note that the range of the scan conditions that can be determined for each X-ray CT apparatus varies.

Next, for cases in which a rotation speed of the gantry is selected at the input part 5a by a tester, etc., the determining part 10 determines the rotation speed of the gantry R, which is selected from the plurality of rotation speeds of the gantry stored in the memory 5f (S21).

Next, for cases in which a frequency of intermittent emission is selected at the input part 5a by a tester, etc., the determining part 10 determines the frequency of intermittent emission Y, which is selected from the plurality of frequencies of intermittent emission stored in the memory 5f (S22). Note that S21 and S22 may be performed simultaneously or the sequence may be reversed.

Next, the first calculating part 12 calculates the interval times Tc based on the rotation speed of the gantry R and the frequency of intermittent emission Y (S23). The relationship between the rotation speed of the gantry, the frequency of intermittent emission, and the interval times is shown in the above Formula (7). That is, as is the case with the first embodiment, utilizing the relationship between the rotation speed of the gantry, the frequency of intermittent emission, and the interval times, it is possible to calculate a desired value (in the present embodiment, interval times).

Next, the acquiring part 11, based on the interval times Tc, acquires the first X-ray emitting condition and the second X-ray emitting condition (S24). As above, based on the interval times calculated at the first calculating part 12, the acquiring part 11 uniquely acquires the first X-ray emitting condition and the second X-ray emitting condition, using the table stored in the memory 5f.

Next, the scan condition determining part 5d calculates the number of X-ray emissions required for the X-ray scanning based on the scan condition selected by a tester, etc. (S25). Note that the number of X-ray emissions may be determined in advance when the scan condition is determined at S10.

Based on the rotation speed of the gantry R determined at S21, the frequency of intermittent emission Y determined at S22, and the number of X-ray emissions determined at S25, the second calculating part 13 calculates the total time (the exposure time [s]) for the X-ray scanning (S26). For the X-ray emitting condition calculated at S24 and the exposure time determined at S26, for example, after they are combined with other test conditions by the display controller, not shown in the figures, they are displayed on the display 6. Therefore, it is possible for the tester to understand the X-ray emitting condition and the exposure time, based on the rotation speed of the gantry and the frequency of intermittent emission, which are determined based on the tester's own selection.

When the tester determines that it is appropriate to conduct a test with the exposure time calculated at S26, the tester performs input action with the input part 5a, providing a command to start the operation of the X-ray CT apparatus 1. Accordingly, as the controller 5b controls the action of the X-ray CT apparatus 1, based on the condition determined from S20 to S26, the dual energy method X-ray scanning is started (S27).

In the above explanation, one frequency of intermittent emission Y is selected and the exposure time, etc., are calculated; however, for example, with respect to any one of the rotation speeds of the gantry, it is possible to determine values of the plurality of frequencies of intermittent emission and calculate the exposure time, etc., with respect to each value.

Moreover, displayed on the display 6 is at least one of the rotation speed of the gantry, the frequency of intermittent emission, the first X-ray emitting condition, the second X-ray emitting condition, and the exposure time.

Moreover, even for cases of half reconstruction, processing in the present embodiment can be executed using Formula (6).

Even for cases in which the rotation speed of the gantry or the frequency of intermittent emission are determined in advance, as is the case with the present embodiment, based on Formula (6) or Formula (7), by calculating the interval times at the first calculating part 12, it is possible to determine the X-ray emitting condition. Therefore, it is possible to display the information on the display 6, making it easy for the tester to determine the exposure condition.

(Common Items for the First and Second Embodiments)

The abovementioned exposure condition processing method of the X-ray CT apparatus and the X-ray CT apparatus may be the helical scanning method or the dynamic volume scanning method.

Moreover, it is also possible to program the above processing details and cause a computer to execute them.

As above, according to the present embodiment, among the processing results of the processor 5c, the exposure conditions necessary for the X-ray scanning can be displayed on the display 6.

Therefore, since a tester is able to arbitrarily select the exposure condition, desired tests can be effectively conducted.

While certain embodiments have been described, these embodiments have been presented by way of example only, and are not intended to limit the scope of the inventions. Indeed, the novel systems described herein may be embodied in a variety of their forms; furthermore, various omissions, substitutions and changes in the form of the systems described herein may be made without departing from the spirit of the inventions. The accompanying claims and their equivalents are intended to cover such forms or modifications as would fall within the scope and spirit of the inventions.

What is claimed is:

1. An exposure condition processing method for an X-ray CT apparatus, comprising:
   a step in which a first X-ray emitting condition for the X-ray CT apparatus and a second X-ray emitting condition, which is different from said first X-ray emitting condition, are input to a processor;
   a step in which said processor, based on said first X-ray emitting condition and said second X-ray emitting condition, acquires interval times for switching a first X-ray scanning with said first X-ray emitting condition, and a second X-ray scanning with said second X-ray emitting condition; and
   a step in which said processor, based on a rotation speed of a gantry in said X-ray CT apparatus that is previously stored in a memory and said interval times, calculates a frequency of intermittent emission of an X-ray, with respect to said rotation speed of the gantry.

2. The exposure condition processing method for the X-ray CT apparatus, according to claim 1, further comprising:
   a step in which said processor, based on said rotation speed of the gantry, said frequency of intermittent emission, and a number of X-ray emissions during X-ray scanning with said X-ray CT apparatus that is previously set, calculates a total exposure time to perform said first X-ray scanning and said second X-ray scanning.

3. The exposure condition processing method for an X-ray CT apparatus, according to claim 2, comprising:
   a step in which said display displays said total exposure time.

4. The exposure condition processing method for the X-ray CT apparatus, according to claim 3, further comprising:
   a priority condition input step for inputting, with respect to said processor, for an X-ray image obtained from said X-ray scanning, whether to select a condition of prioritizing contrast or a condition of prioritizing time resolution;
   wherein, displayed on said display, is at least one of said rotation speed of the gantry, said frequency of intermittent emission, said first X-ray emitting condition, said second X-ray emitting condition, and said total exposure time, corresponding to the condition input by said priority condition input step.

5. An exposure condition processing method for an X-ray CT apparatus, comprising:
   a step in which a rotation speed of a gantry in an X-ray CT apparatus is input to a processor;
   a step in which a frequency of intermittent emission that is set with respect to said rotation speed of the gantry is input to said processor;
   a step in which said processor, based on said set rotation speed of the gantry and said frequency of intermittent emission, calculates interval times for switching a first X-ray scanning with a first X-ray emitting condition, and a second X-ray scanning with a second X-ray emitting condition, which is different from said first X-ray emitting condition; and
   a step in which said processor, based on said interval times, acquires said first X-ray emitting condition and said second X-ray emitting condition.

6. The exposure condition processing method for the X-ray CT apparatus, according to claim 1 or claim 5, further comprising:
   a step in which a display of said X-ray Ct apparatus displays at least one of said rotation speed of the gantry, said frequency of intermittent emission, said first X-ray emitting condition, and said second X-ray emitting condition.

7. An X-ray CT apparatus, comprising:
   a bed on which a subject is disposed;
   a gantry configured to include an X-ray emitting part that emits an X-ray and an X-ray detector that detects said X-ray that penetrates through said subject;
   an input part;
   a determining part that, based on the input by said input part, determines a first X-ray emitting condition for said X-ray emitting part, and a second X-ray emitting condition, which is different from said first X-ray emitting condition;
   an acquiring part that, based on said first X-ray emitting condition and said second X-ray emitting condition, which are determined by said determining part, acquires interval times for switching a first X-ray scanning with said first X-ray emitting condition, and a second X-ray scanning with said second X-ray emitting condition; and
   a first calculating part that, based on a rotation speed of said gantry that is stored previously in a memory and said interval times, calculates a frequency of intermittent emission of the X-ray, with respect to said rotation speed of the gantry.

8. The X-ray CT apparatus according to claim 7, comprising:
   a second calculating part that, based on said rotation speed of the gantry, said frequency of intermittent emission, and a number of X-ray emissions during X-ray scanning with said X-ray CT apparatus that is previously set, calculates a total exposure time to perform said first X-ray scanning and said second X-ray scanning.

9. The X-ray CT apparatus according to claim 8, wherein said display displays said total exposure time.

10. The X-ray CT apparatus according to claim 9, further comprising:
    a priority condition selecting part that, based on the input by said input part, for an X-ray image obtained from said X-ray scanning, selects a condition of prioritizing contrast or a condition of prioritizing time resolution,
    wherein, displayed on said display, is at least one of said rotation speed of the gantry, said frequency of intermittent emission, said first X-ray emitting condition, said second X-ray emitting condition, and said total exposure time, corresponding to the condition selected by said priority condition selecting part.

11. An X-ray CT apparatus, comprising:
    a bed on which a subject is disposed;
    a gantry configured to include an X-ray emitting part that emits an X-ray and an X-ray detector that detects said X-ray that penetrates through said subject;
    an input part;
    a determining part that, based on the input by said input part, determines a rotation speed of said gantry and a frequency of intermittent emission;
    a first calculating part that, based on said rotation speed of the gantry and said frequency of intermittent emission, calculates interval times for switching a first X-ray scanning with a first X-ray emitting condition, and a second X-ray scanning with a second X-ray emitting condition, which is different from said first X-ray emitting condition; and
    an acquiring part that, based on said interval times, acquires said first X-ray emitting condition and said second X-ray emitting condition.

12. The X-ray CT apparatus according to claim 7 or claim 11, comprising:
   a display that can display at least one of said rotation speed of the gantry, said frequency of intermittent emission, said first X-ray emitting condition, and said second X-ray emitting condition.

13. The X-ray CT apparatus according to claim 11, comprising:
   a second calculating part that, based on said rotation speed of the gantry, said frequency of intermittent emission, and the number of X-ray emissions during X-ray scanning with said X-ray CT apparatus that is previously set, calculates the total exposure time to perform said first X-ray scanning and said second X-ray scanning.

14. The X-ray CT apparatus according to claim 13, wherein said display displays said total exposure time.

15. The X-ray CT apparatus according to claim 14, further comprising:
   a priority condition selecting part that, based on the input by said input part, for an X-ray image obtained from said X-ray scanning, selects a condition of prioritizing contrast or a condition of prioritizing time resolution,
   wherein, displayed on said display, is at least one of said rotation speed of the gantry, said frequency of intermittent emission, said first X-ray emitting condition, said second X-ray emitting condition, and said total exposure time, corresponding to the condition selected by said priority condition selecting part.

\* \* \* \* \*